United States Patent [19]

Wagman et al.

[11] Patent Number: 4,551,330
[45] Date of Patent: Nov. 5, 1985

[54] SKIN AND HAIR CONDITIONER COMPOSITIONS AND CONDITIONING METHOD

[75] Inventors: Julius Wagman; Branko Sajic, both of Chicago, Ill.

[73] Assignee: Helene Curtis Industries, Inc., Chicago, Ill.

[21] Appl. No.: 509,642

[22] Filed: Jun. 30, 1983

[51] Int. Cl.$^4$ .......... A61K 7/06; A61K 7/08; A61K 7/42; A61K 7/44

[52] U.S. Cl. .......... 424/59; 132/7; 252/309; 424/65; 424/66; 424/67; 424/68; 424/70; 424/73; 514/943; 514/786

[58] Field of Search .......... 424/70, 365, 59, 65, 424/66, 67, 68, 73; 132/7; 252/309

[56] References Cited

U.S. PATENT DOCUMENTS

| 2,210,014 | 8/1940 | Teller | 424/65 |
| 3,343,530 | 9/1967 | Solees et al. | 132/9 X |
| 4,210,161 | 7/1980 | Wagman | 424/DIG. 2 |

FOREIGN PATENT DOCUMENTS

| 0059882 | 9/1982 | European Pat. Off. | 424/68 |
| 1251467 | 10/1967 | Fed. Rep. of Germany | 424/68 |
| 2454692 | 5/1976 | Fed. Rep. of Germany | 424/65 |
| 3015868 | 11/1980 | Fed. Rep. of Germany | 424/70 |
| 0061238 | 5/1977 | Japan | 424/68 |
| 0076439 | 6/1977 | Japan | 424/365 |
| 0095109 | 8/1981 | Japan | 424/365 |
| 0095108 | 8/1981 | Japan | 424/365 |

Primary Examiner—Dale K. Ore
Attorney, Agent, or Firm—Dressler, Goldsmith, Shore, Sutker & Milnamow, Ltd.

[57] ABSTRACT

Compositions are disclosed for providing non-greasy, cosmetic moisturizing, conditioning and protective barrier effects on skin and hair, and to a rinse-on method for producing these effects. More particularly the compositions comprise oil-in-water emulsions that are adapted to invert to water-in-oil emulsions at the hair or skin surface when they are rubbed into the skin and hair. The compositions a include water, unctrous oleaginous material, water-dispersible, non-toxic polyvalent metal salt having a cation selected from the group consisting of aluminum (III), cerium (III), iron (III), zirconium (IV), aluminum zirconium coordination complexes, and mixtures thereof and sufficient acid or alkali to provide a pH value of about 1.5 to 7.5.

20 Claims, No Drawings

SKIN AND HAIR CONDITIONER COMPOSITIONS AND CONDITIONING METHOD

TECHNICAL FIELD

This invention relates to compositions for providing nongreasy, cosmetic moisturizing, conditioning and protective barrier effects on skin and on hair, and to a method for producing these effects.

BACKGROUND ART

Cosmetic conditioner compositions for moisturizing and providing protective barrier films on the skin are known in the art and are in daily use by consumers. Typically commercially available compositions are comprised of oil-in-water emulsions that are easily rinsed from the skin by soap and water and frequently by water alone. Therefore, the consumer must apply such compositions frequently in order to maintain any semblance of lasting moisturizing and conditioning effects.

Some attempts have been made to provide greater conditioning effects by means of water-in-oil type emulsions but these compositions leave a slippery, oily feel on the skin that is usually interpreted as "greasy" to the consumer. This greasy effect is cosmetically undesirable to the touch in a skin product and, in a hair product, it imparts a soiled appearance to the hair, frequently making the hair limp.

One of the main reasons consumers use moisturizing, conditioning compositions that provide protective barriers on the skin and hair is to protect against chemical and environmental hazards to which their bodies are exposed in the home and in the workplace. Compositions that are too easily rinsed from the skin during the normal course of the day do not provide continuous protection. Products that are too greasy are unattractive to the user, no matter how effective they may be, because they are cosmetically and aesthetically unappealing.

A desirable product, therefore, would provide a nongreasy, cosmetically pleasing, moisturizing, conditioning effect and yet provide a protective barrier, be easy to apply and resist removal when the skin or hair is rinsed with water.

BRIEF SUMMARY OF THE INVENTION

In one aspect of this invention, there is provided a cosmetic composition for use on skin and hair comprising an oil-in-water emulsion including about 70 to about 90 weight percent water, about 5 to about 25 weight percent water-insoluble, unctuous, oleaginous material, about 0.5 to about 7 weight percent water-dispersible emulsifying agent, about 0.05 to about 3.0 weight percent water-dispersible, non-toxic polyvalent metal salt having a cation selected from the group consisting of aluminum (III), cerium (III), iron (III), zirconium (IV), aluminum zirconium coordination complexes and mixtures thereof, and sufficient acid or alkali to provide a pH value of about 1.5 to about 7.5. The water-dispersible emulsifying agents used in the cosmetic composition are materials which do not form true solutions in water and are selected from the group consisting of non-ionic and cationic emulsifiers, and mixtures thereof. The emulsifying agent may include a water-soluble non-ionic material. The cosmetic composition is adapted to invert to a water-in-oil type emulsion at the skin or hair surface when it is rubbed into the skin or the hair without producing the unappealing greasy effect normally associated with water-in-oil type emulsion products. Excess water, beyond what is held in the surface water-in-oil emulsion, forms a separate outer layer which is rinsed, rubbed or evaporated away, or which may be towel blotted.

A cosmetic composition of this invention provides a long-lasting cosmetically aesthetic, moisturizing and conditioning effect, as well as a skin protective barrier coating. A composition of this invention can be applied by means of a rinse-on method comprising the steps of rubbing the composition into wet skin or wet hair and then rinsing the treated skin or hair with water. In a rinse-on method the composition deposits a non-greasy coating on the skin or hair that provides a water-resistant barrier film. Heretofore this could be achieved only with heavy greasy compositions which were cosmetically unappealing. Alternatively, a cosmetic composition of this invention can be rubbed directly into dry skin or dry hair in the usual manner to deposit a barrier coating against water and water-soluble materials.

A distinct advantage of the compositions of this invention is that a discernible amount of conditioning and emollient material deposits on the skin in a single application on the oil-in-water emulsion. The level of cosmetic effects produced would normally require multiple or repeated applications of this type of emulsion. Oil-in-water emulsion compositions are usually preferred because they are easily prepared, provide a cooling effect on the skin and are generally more appealing to the consumer. Thus, the benefit of an oil-in-water emulsion system is maintained by the cosmetic compositions of this invention while providing the conditioning benefits normally associated only with water-in-oil type emulsions.

The barrier film deposited on the skin is particularly beneficial for protecting it from skin irritants, such as dusts, soils, and the like present in the home and workplace environment.

The inversion of the compositions from oil-in-water to water-in-oil emulsions at the hair surface provides an added benefit for conditioning dry hair. Hair can become dry looking and straw-like as a result of being frequently treated with chemical products, such as waving and dyeing. As currently practiced in the art, attempts to condition such hair are made by means of well-known "hot oil" treatment. Conventional hot oil treatments use heavy oils that are difficult to remove and cosmetically unpleasant. The compositions of this invention provide a cosmetically elegant product for use in place of the oils to achieve the same effect.

Another advantage is that oil-soluble materials that are cosmetically or therapeutically desirable, such as sunscreens, fungicides, antibactericides, keratolytic agents, vitamins, fragrances, and pigments, can be deposited on the skin or hair in a water-insoluble coating. This advantage is particularly beneficial because it can be achieved even when the skin or hair is wet.

Still further benefits and advantages of the present invention will become apparent to those skilled in the art from the detailed description of the invention, the examples and the claims which follow.

DISCLOSURE OF THE INVENTION

A cosmetic composition is disclosed comprising an oil-in-water (o/w) emulsion that is adapted to invert to a water-in-oil emulsion (w/o) when the composition is rubbed into skin and hair to provide a moisturizing, conditioning protective barrier coating on the skin and hair. The composition is as easy to prepare as a conventional o/w emulsion. It provides a level of moisturizing, conditioning and protective barrier effects normally associated with w/o type emulsions, while overcoming the normally objectionable greasy feel associated with the latter. This novel conditioning cosmetic composition comprises:

(a) from about 70 to about 90 weight percent water;

(b) from about 5 to about 25 weight percent water-insoluble, unctuous oleaginous material;

(c) about 0.1 to about 7 weight percent water-dispersible emulsifying agent selected from the group consisting of non-ionic and cationic emulsifiers, and mixtures thereof. A water-soluble non-ionic emulsifier may be included having an HLB value greater than 8, as determined by the well-known Hydrophile-Lipophile Balance (HLB) system;

(d) from about 0.05 to about 3.0 weight percent water-dispersible, non-toxic polyvalent metal salt having a cation selected from the group consisting of aluminum (III), cerium (III), iron (III), zirconium (IV), aluminum zirconium coordination complexes and mixtures thereof; and (e) sufficient acid or alkali to provide a pH value of about 1.5 to about 7.

The unusual conditioning effects, especially rinse-off conditioning, produced by the compositions are attributed to the presence of the water-dispersible polyvalent metal salt in the emulsion. Particularly preferred polyvalent salts are:

(a) aluminum chloride hexahydrate present in amounts of from 0.05 to about 3 weight percent in a composition having a pH value in a range of from about 1.5 to about 5;

(b) complex basic aluminum chloride loosely hydrated with about 2.5 moles of water, commonly referred to as aluminum chlorohydrate, present in amounts of from 0.06 to about 2.5 weight percent in a composition having a pH value in a range of from 4.2 to about 5.6;

(c) a loosely hydrated coordination complex of aluminum zirconium chlorohydrate, including the tri-, tetra- and pentachlorohydrate, and glycine complexes thereof, present in amounts of from 0.51 to about 1.3 weight percent in a composition having a pH value in a range of from 4.3 to about 7.0;

(d) zirconium (IV) oxychloride octahydrate present in amounts of 0.13 to about 1.3 weight percent in a composition having a pH value in a range of from 1.6 to about 5.6;

(e) iron (III) nitrate nonahydrate present in amounts of from 0.17 to about 1.7 weight percent in a composition having a pH value in a range of from 1.8 to about 6.5; and (f) cerium (III) nitrate hexahydrate present in amounts of from 0.5 to about 4.0 weight percent in a composition having a pH value in a range of from 2.3 to about 7.5.

Exemplary aluminum, zirconium and aluminum zirconium complexes are described in the *CTFA Cosmetic Ingredient Dictionary*, 3rd Edition, published by the Cosmetic, Toiletry and Fragrance Association, Inc., incorporated herein by reference. Particularly preferred materials are commercially available under the trademarks, Rezal, Chlorhydrol, and Rehydrol sold by the Reheis Chemical Company.

The cosmetic compositions of this invention are prepared by generally known techniques for preparing o/w emulsions described below in Example 2. Briefly described, the general procedure is as follows; the aqueous phase (I) is heated to about 80 degrees C. (about 175 degrees F.) in a separate vessel from the oil phase (II). The oil phase comprises the oleaginous materials, emulsifiers, oil-soluble preservatives, and any additional oil soluble or oil dispersible cosmetic ingredients. The oil phase is heated to about 82 degrees C. (about 180 degrees F.), and added slowly with agitation to the heated water phase (I). After continued agitation and maintenance of the temperature at about 80 degrees C. (about 175 degrees F.), the composition is cooled to about 49 degrees C. (about 120 degrees F.). At this temperature the fragrance phase (III) is added. The fragrance phase may include additional preservative, fragrance emulsifiers and heat-sensitive ingredients if needed. At this temperature the polyvalent salt phase (IV) comprising a water solution of a polyvalent salt is also added to the batch. The emulsion is mixed further and an acid or alkaline phase (V) comprising an aqueous solution of acid or alkaline caustic material is added to adjust the pH value of the composition. The emulsion is mixed further and cooled to about 32 degrees C. (about 90 degrees F.) and stored in containers until ready for use.

It is to be understood that the term "conditioning" as used herein is intended to include moisturizing and protective barrier coating effects by reference. It is also to be understood that the terms "composition" and "cosmetic composition" will be used interchangeably with the term "emulsion" to denote an o/w emulsion that inverts to a w/o emulsion at the hair and skin surface when it is subjected to frictional shear by being rubbed onto and into the skin or hair. It is further to be understood that the terms "conditioned skin" or "conditioned hair" denotes skin or hair that has been treated with a composition of this invention by means of the rinse-on or rub-on methods described below.

The oleaginous material is selected from known cosmetic unctuous materials. It is to be understood that the terms "oleaginous" and "unctuous" includes materials that are, themselves, water-insoluble and require emulsifying agents to disperse them in water but which may, themselves, function as emulsifying agents. Suitable materials are illustrated, without limitation by mineral hydrocarbon waxes, greases and oils, animal fats and greases, plant waxes, saturated and unsaturated vegetable, animal and plant oils, hydrogenated and unhydrogenated unsaturated oils, waxes and fats, cosmetic silicone fluids such as a linear polysiloxane polymer, an olefinic ester of saturated fatty acid, and mixtures thereof. Particularly preferred oleaginous materials include petrolatum, liquid paraffin, lanolin, lard, jojoba oil, corn oil, peanut oil, olive oil, mink oil, soybean oil, hydrogenated triglycerides, such as Crisco, sold under that trademark by the Procter & Gamble Company, beeswax, hydrogenated jojoba oil, tallow, isopropyl myristate, stearyl alcohol, cetyl alcohol, mineral oil, glyceryl stearate, and the like. While the oleaginous materials may be present at about 5 to about 25 weight percent, persons skilled in the art will appreciate that the actual amount used in a product is determined by the desired product consistency and level of conditioning effect.

A particular advantage of this invention is that the o/w emulsions can be prepared using small amounts of emulsifiers. For example, emulsions can be prepared with less than 5 weight percent emulsifying agent. The compositions are preferably prepared using water-dispersible non-ionic and cationic emulsifiers, and mixtures thereof. The selection of the emulsifier adapts the o/w emulsion for inversion to a w/o emulsion under frictional pressure when it is rubbed into skin and hair, preferably onto wet skin and wet hair.

Commercially available cationic emulsifiers are well known in the art. Suitable cationic emulsifiers may be illustrated without limitation by quaternized ammonium bromide and chloride salts and mixtures thereof. A preferred cationic emulsifier is cetyltrimethylammonium chloride. Preferably, the concentration of the cationic emulsifier is about 1 to about 2 weight percent, more preferably about 1.5 to 1.8 weight percent. Cationic emulsifiers are believed to augment the overall conditioning effects because of their well known substantivity to keratin substrates such as skin and hair.

Non-ionic emulsifiers are also well known in the art and are commercially available. The type of non-ionic emulsifier selected depends on the hydrophile-lipophile balance (HLB) needed to emulsify the oleaginous material. The method of calculating the HLB value is well known in the art. The HLB of the non-ionic emulsifying agent in the emulsion is selected to fall in a range of about 6 to about 16, preferably between about 6 to about 10. Water-dispersible emulsifying agents denote materials that produce a milky dispersion in water at an HLB value of from about 6 to about 10. The amount of water-dispersible non-ionic emulsifying agent is about 0.5 to about 7 weight percent selected from the group consisting of lipophilic non-ionic and cationic emulsifiers having an individual HLB value of about 4 to about 6. The emulsifying agent may include a highly water-soluble non-ionic material that is one having an individual HLB value greater than 8. However, its concentration is preferably kept to a level of about 0.1 to about 0.5 weight percent. Higher concentrations of highly water-soluble non-ionic emulsifiers, however, may be used in combination with water-dispersible non-ionic emulsifiers, so long as the calculated HLB value of the emulsifying agent in the emulsion falls in the range of from about 6 to about 10.

Non-ionic emulsifiers may be exemplified, without limitation, by polyoxyethylene ethers of fatty alcohols such as polyoxyethylene (20) cetyl ether, polyoxyethylene (2) oleyl ether, polyoxyethylene (15) nonylphenyl ether and the like, sorbitan stearate, glyceryl stearate, $C_{12}$–$C_{18}$ fatty alchohols, esters and ethers thereof.

Conventional water-soluble anionic wetting agents such as sodium lauryl sulfate, and water-soluble betaine-type amphoteric wetting agents are not included in the compositions of this invention because they have been found to interfere with the conditioning effects otherwise obtained.

Other ingredients may also be included in the compositions selected from among known materials for their conventionally employed purposes. These include fragrances, coloring agents, preservatives, and thickeners.

Persons skilled in the art will appreciate that the compositions of this invention can be rubbed onto dry skin and dry hair and allowed to dry in the usual manner. What is surprising, however, is that a conditioning, moisturizing and protective barrier coating can be deposited on the skin from a rinse-on application, as described below. Particularly surprising is that the compositions invert from oil-in-water emulsions to water-in-oil emulsions at the skin or hair surface when they are rubbed into wet skin and wet hair. The outer layer of excess moistures dries rapidly on the skin and the inverted emulsion forms a coating which is a barrier to water and water-soluble materials. The coating is discernible to the touch but is non-greasy in most applications. However, if a coating with a greasy feel is desired, the compositions of the invention may be formulated to produce such a feel, as described below.

The mechanism by which the compositions of this invention invert to form water-in-oil emulsions is not understood.

The composition of this invention provides a unique means for depositing and adhering therapeutically active skin care material to the skin, such as fungicides for athlete's foot, such as zinc undecylenate and undecylenic acid, antimicrobials for acne, keratolytic agents for foot callouses and corns, anti-dandruff agents and the like. Such products are usually either applied to carefully dried skin or are rinsed away with water. The compositions of this invention can be applied to the skin and rinsed on during the normal course of the user's ablutions. This benefit is particularly valuable for maintaining fungicidal athlete's foot agents in contact with the affected area, without resorting to using greasy ointments that stain the stockings or to vehicles that are washed away by perspiration or water during the course of the day. Further, the known astringent properties of some of the aluminum and zirconium salts may provide an added benefit of inhibiting perspiration in combination with the antifungal activity.

The compositions of this invention also provide a novel vehicle for applying bath oils and after-bath products, such as talcum powder. This benefit is particularly useful as a means of depositing bath oil materials, such as isopropyl myristate, on the skin during the course of a shower bath. Likewise, talcum powder may be included in the composition to deposit a bath powder or after-shave powder finish on the skin. Similarly, pigments may be included in a composition of this invention to provide visually opaque coatings on the skin that are not washed away by normal perspiration or water. These coatings are particularly useful as opaque sunblocks for the skin and as opaque makeup compositions for hiding blemishes on the face and body or as opaque makeup for the legs.

The compositions of this invention can be prepared in the form of lotions and creams.

If it is desired to produce a film with an oily or greasy feel, comparable in hair dessing to the application of a pomade, such an effect may be obtained by appropriate selection of the nature and amount of the water-insoluble, unctuous oleaginous material. For an oily film, the unctuous oleaginous material should be present at a level of at least 15 weight percent and at least 50% of the unctuous oleaginous materials should be a normally solid material, such as petrolatum.

This invention is further illustrated in the following examples, which are not intended to be limiting.

BEST MODES FOR CARRYING OUT THE INVENTION

A. Methods of Application For Conditioning

In the examples described below, rinse-on and rub-on procedures, using a composition of this invention, are employed to provide cosmetically elegant moisturizing, conditioning, protective barrier effects on skin and on hair. The general methods for employing these rinse-on and rub-on procedures are described immediately herebelow.

1. Rinse-on Method A

Wash the skin area or hair to be conditioned with a commercially available liquid detergent containing synthetic surfactants, and commonly referred to as a "liquid soap". The washing procedure consists of wetting of the skin or hair with water, applying the liquid soap and washing the skin or hair in the usual manner. The liquid soap is rinsed from the skin or hair with water.

For skin conditioning, the still-wet skin is treated with the composition by rubbing it onto the wet skin and spreading it over the entire area. The skin is then thoroughly rinsed with water and patted lightly with a towel to dry.

For hair conditioning, the wet hair is lightly towel blotted to remove excess water and the composition is rubbed onto the wet hair and distributed thoroughly to coat the fibers. The hair is then rinsed with water and dried in the usual manner.

2. Rinse-on Method B

The same washing and conditioning procedure as in Rinse-On Method A is followed, except that Ivory soap, sold under this trademark by the Procter & Gamble Company, is used in place of the liquid soap.

For both Rinse-on Method A and Rinse-on Method B, the water used may be soft water, including distilled or deionized water, or hard water.

3. Rub-on Method

A conditioner composition is rubbed onto dry skin or dry hair and thoroughly rubbed into the skin or hair to provide a barrier coating.

Conditioning and moisturizing effects are evaluated by feeling the treated skin area for smooothness discernible to the touch. Evaluation of protective barrier effects are described in Examples 5 and 14.

B. Glossary of Materials

In the following examples certain components of the composition are referred to, for easy reference and convenience, by their commercial trademark or CTFA name as provided immediately herebelow.

(a) Silicone 200 Fluid, trademark of Dow Corning Corporation is a mixture of fully methylated linear siloxane polymers end blocked with trimethylsiloxy units. CTFA name: Dimethicone.

(b) Lanolin AAA is deodorized anhydrous lanolin U.S.P., CTFA name: Lanolin.

(c) Stearic acid xxx is a triple pressed grade of stearic acid.

(d) Lipocol C-20, trademark of Lipo Chemicals, Inc. for polyoxyethylene (20) cetyl ether. CTFA name: Ceteth-20. HLB value about 15 to 17.

(e) Cetrimonium Chloride: CTFA name for Cetyltrimethyl ammonium chloride.

(f) Amphosol CA, trademark of Stepan Chemical for CTFA name: Cocamidopropylbetaine.

(g) Span 60, trademark of ICI United States, Inc. for CTFA name: Sorbitan stearate. HLB value about 4 to 6.

(h) Brij 92, trademark of ICI United States, Inc. for polyoxythylene (2) oleyl ether CTFA name: Oleth-2. HLB value about 4–6.

(i) Igepal CO-730, trademark of GAF Corporation for polyoxyethylene (15) nonyl phenyl ether. CTFA name: nonoxynol 15. HLB value about 13.

C. Preparation of Emulsions

The general procedure for preparing the emulsions consists of the steps of (1) heating the components of Phase I in a mixing vessel containing a high speed mixer to a temperature of about 80 degrees C. (175 degrees F.); (2) combining, in a separate vessel, the components of Phase II with stirring and heating to about 82 degrees C. (180 degrees F.); (3) adding Phase II to Phase I with good agitation; (4) maintaining agitation for 30 minutes while holding the batch temperature at about 80 degrees C. (175 degrees F.); (5) cooling the batch slowly to about 49 degrees C. (120 degrees F.); (6) adding the components of Phase III to the batch at 49 degrees C. (120 degrees F.); adding the premixed components of Phase IV, mixing well; (8) adding the premixed components of Phase V; (9) cooling the batch to about 32 degrees C. (90 degrees F.); and packaging the composition in bottles. It is to be understood that the following compositions are prepared as described.

EXAMPLE 1

Comparison of Emulsifiers in An Aluminum-Containing Rinse-on Cosmetic Composition This example shows the effectiveness of water-dispersible non-ionic and cationic materials as emulsifying agents in rinse-on compositions in contrast to water-soluble anionic and amphoteric wetting agents.

The components of exemplary compositions containing aluminum salt are shown in Formulations A, B, C and D below. Each emulsion is adjusted to about pH 4.0 with sodium hydroxide. The non-ionic emulsifier in Formula A is LIPOCOL C-20; the cationic emulsifier in Formula B is cetrimonium chloride; the anionic emulsifier in Formula C is sodium lauryl sulfate and the amphoteric emulsifier in Formula D is Amphosol CA as previously identified in the glossary.

| Component | Weight Percent in Formula | | | |
|---|---|---|---|---|
| | A | B | C | D |
| Phase I: | | | | |
| Deionized water | 75.140 | 73.600 | 73.600 | 74.050 |
| Phase II: | | | | |
| Petrolatum | 9.850 | 9.850 | 9.850 | 9.850 |
| Mineral oil, 65/75 visc. | 7.450 | 7.450 | 7.450 | 7.450 |
| Methylparaben | 0.150 | 0.150 | 0.150 | 0.150 |
| Silicone 200 Fluid, 350 cps | 0.650 | 0.650 | 0.650 | 0.650 |
| Propylparaben | 0.100 | 0.100 | 0.100 | 0.100 |
| Glycerylstearate | 2.600 | 2.600 | 2.600 | 2.600 |
| Lanolin AAA | 0.650 | 0.650 | 0.650 | 0.650 |
| Cetyl alcohol | 1.950 | 1.950 | 1.950 | 1.950 |
| Stearic acid XXX | 0.125 | 0.125 | 0.125 | 0.125 |
| Non-ionic emulsifier | 0.180 | | | |
| Cationic emulsifier | | 1.720 | | |
| Anionic emulsifier | | | 1.720 | |
| Amphoteric emulsifier | | | | 1.700 |
| Phase III: | | | | |
| Fragrance | 0.200 | 0.200 | 0.200 | 0.200 |
| 1,3 Dimethylol-5,5-dimethyl hydantoin | 0.250 | 0.250 | 0.250 | 0.250 |
| Phase IV: | | | | |
| Aluminum chloride hexahydrate | 0.300 | 0.300 | 0.300 | 0.300 |
| Deionized water | 0.300 | 0.300 | 0.300 | 0.300 |
| Phase V: | | | | |
| Sodium hydroxide (50% in water) | 0.105 | 0.105 | 0.105 | 0.125 |
| | 100.00 | 100.00 | 100.00 | 100.00 |
| pH | 3.93 | 4.00 | 4.00 | 4.00 |

-continued

| Component | Weight Percent in Formula | | | |
|---|---|---|---|---|
| | A | B | C | D |
| Appearance of Emulsion on Standing | Homogeneous | | Separate into two layers | |

In separate tests, using 4 female volunteers, one hand is treated with one of the compositions by Rinse-on Method A and the other hand is treated with the same composition by Rinse-On Method B of Example 1. Each volunteer is treated with a different composition. Compositions A and B provide a discernible conditioning, moisturizing effect on the skin. Compositions C and D produce no discernible conditioning, moisturizing effects.

The rinsed-on conditioning on the skin of the hands is nongreasy to the touch even though the emulsion inverts from an oil-in-water (o/w) emulsion to a water-in-oil (w/o) emulsion. Inversion is demonstrated after treating the skin by Rinse-on Method A by scraping the coating from the wet skin with a glass microscopic slide. A portion of the scraped coating from the microscopic slide is then immersed in water and another portion is immersed in light mineral oil. The scraping disperses in the oil but not in the water.

EXAMPLE 2

Effect of pH on Rinse-on Conditioning of An Aluminum-containing Composition

The following series of six separate emulsions (A, B, C, D, E, F) is prepared using the procedure of Example 1, except that each completed composition varies in pH value over a range of from 3.2 to 7.0 by adjusting the amounts of sodium hydroxide in Phase V and the water in Phase I accordingly as needed.

| Component | Weight Percent in Formula |
|---|---|
| Phase I: | |
| Deionized water to 100 g | q.s. |
| Phase II: | |
| Petrolatum | 9.850 |
| Mineral oil, 65/75 visc. | 7.450 |
| Methylparaben | 0.150 |
| Silicone 200 Fluid, 350 cps | 0.650 |
| Propylparaben | 0.100 |
| Glycerylstearate | 2.600 |
| Lanolin AAA | 0.650 |
| Cetyl alcohol | 1.950 |
| Lipocol C-20 | 0.180 |
| Phase III: | |
| Fragrance | 0.200 |
| 1,3 Dimethylol-5,5-dimethyl Hydantoin | 0.250 |
| Phase IV: | |
| Aluminum chloride hexahydrate | 0.300 |
| Deionized water | 0.300 |
| Phase V: | |
| Sodium hydroxide (50% in water) to pH of formula A, B, C, D, E, F, shown below. | q.s. |

The effect of pH value on discernible conditioning effects of each aluminum-containing emulsion is shown below as evaluated by Rinse-on Method A, using soft water, and Rinse-on Method B, using hard water, on the skin of the hands.

| Emulsion | pH | Amount of Discernible Conditioning Coating on Skin of Hands | |
|---|---|---|---|
| | | Rinse-On Method A | Rinse-On Method B |
| A | 3.2 | heavy | heavy |
| B | 4.0 | heavy | heavy |
| C | 4.5 | heavy | heavy |
| D | 5.0 | very light | light |
| E | 6.0 | none[a] | very light |
| F | 7.0 | none[a] | very light |

[a]No coating detected to the touch but the skin repels water.

The data show that the amount of discernible coating depositing on the skin from Emulsion A is greatest between about pH 3.2 and 5.0. Although the amount of physically discernible coating lessens as the pH value of the Emulsion increases to pH 7.0, some protective barrier effect is detectable as an increase in the skin's water repellancy even from Rinse-on Method A, using soft water.

EXAMPLE 3

Rinse-on Sunscreen

The Emulsion B of Example 2 is prepared except that 3% sunscreen material is included in Phase II, and the water content of Phase I is reduced accordingly. The sunscreen is 2-ethoxyethyl-p-methoxycinnamate sold under the trademark Giv-Tan F by Givaudan Corporation. CTFA name: Cinoxate.

The emulsion deposits a water-repellant conditioning coating on the skin of the hands when it is applied by Rinse-on Method A with soft water and by Rinse-on Method B with hard water.

EXAMPLE 4

Evauation of Skin Protective Barrier Coating of Aluminum-containing Conditioner

This example demonstrates the rinse-on protective barrier coating and conditioning effect on skin from a cosmetic emulsion (A) containing an aluminum salt at pH 4.0 by means of a fluorescent technique in accordance with the method described by M. E. Stolar, J. Soc. Cosmetic Chem. 17, 607–621 (1966). The vitamin A palmitate component is also a known fluorescent indicator. For comparison, a counterpart emulsions (B) and (C) is prepared without aluminum salt at near neutral pH and at pH 4.0 respectively.

| Component | Weight Percent in Formula | | |
|---|---|---|---|
| | A | B | C |
| Phase I: | | | |
| Deionized water | 73.278 | 74.720 | 74.650 |
| Phase II: | | | |
| Petrolatum | 11.850 | 11.850 | 11.850 |
| Mineral oil, 65/75 visc. | 5.450 | 5.450 | 5.450 |
| Methylparaben | 0.150 | 0.150 | 0.150 |
| Silicone 200 Fluid, 350 cps | 0.650 | 0.650 | 0.650 |
| Propylparaben | 0.100 | 0.100 | 0.100 |
| Glycerylstearate | 2.600 | 2.600 | 2.600 |
| Cetyl alcohol | 1.950 | 1.950 | 1.950 |
| Lanolin AAA | 0.650 | 0.650 | 0.650 |
| Vitamin A palmitate | 1.000 | 1.000 | 1.000 |
| Stearic acid XXX | 0.250 | 0.250 | 0.250 |
| Lipocol C-20 | 0.180 | 0.180 | 0.180 |
| Phase III: | | | |
| Fragrance | 0.200 | 0.200 | 0.200 |
| 1,3 Dimethylol-5,5-dimethyl hydantoin | 0.250 | 0.250 | 0.250 |
| Phase IV: | | | |

-continued

| | Weight Percent in Formula | | |
|---|---|---|---|
| Component | A | B | C |
| Aluminum chloride hexahydrate | 0.600 | — | — |
| Deionized water | 0.600 | — | — |
| Phase V: | | | |
| Citric acid (50% in water) | — | — | 0.070 |
| Sodium hydroxide (50% in water) | 0.242 | | |
| | 100.000 | 100.000 | 100.000 |
| pH | 3.93 | 7.20 | 4.00 |

When the skin of hands is treated with Emulsion A by Rinse-on Method A and by Rinse-on method, B a coating deposits on the skin that fluoresces when the skin is viewed under an ultra-violet light source. When the skin of the hands is similarly treated with either Emulsion B or C no fluorescence is observed.

EXAMPLE 5

Rinse-on Hair Conditioner

This example shows the conditioning effect of a hair conditioner containing an aluminum salt by means of a colorimetric test. The following emulsion (A) is prepared with aluminum salt and a counterpart emulsion (B), without aluminum salt, is also prepared for comparison.

| | Weight Percent in Formula | |
|---|---|---|
| Component | A | B |
| Phase I: | | |
| Deionized water | 74.280 | 75.720 |
| Phase II: | | |
| Petrolatum | 11.850 | 11.850 |
| Peanut Oil | 5.450 | 5.450 |
| Methylparaben | 0.150 | 0.150 |
| Silicone 200 Fluid, 350 cps | 0.650 | 0.650 |
| Propylparaben | 0.100 | 0.100 |
| Glycerylstearate | 2.600 | 2.600 |
| Lanolin AAA | 0.650 | 0.650 |
| Cetyl alcohol | 1.950 | 1.950 |
| Stearic acid XXX | 0.250 | 0.250 |
| Lipocol C-20 | 0.180 | 0.180 |
| Phase III: | | |
| Fragrance | 0.200 | 0.200 |
| 1,3 Dimethylol-5,5-dimethyl hydantoin | 0.250 | 0.250 |
| Phase IV: | | |
| Aluminum chloride hexahydrate | 0.600 | — |
| Deionized water | 0.600 | — |
| Phase V: | | |
| Sodium hydroxide (50% in water) | 0.240 | — |
| | 100.000 | 100.000 |
| pH | 4.00 | 6.60 |

A tress of naturally blonde human hair (De Meo Brothers, New York), about 6 inches long and 2 grams in weight, is treated with Emulsion A by Rinse-on Method B with hard water. The treated tress is then treated with osmic acid using the method described by H. T. Spoor in Amer. Pract. D.T., 11:497–505 (1960) incorporated herein by reference. A pronounced black stain develops on the hair. On the other hand when a second tress is similarly treated with Emulsion B, no stain develops showing that no oil-containing film deposits.

EXAMPLE 6

The Effect of Rinse-on Conditioning of Various Concentrations of Aluminum Chloride This example shows the conditioning effects produced by varying concentrations from 0.05 to about 6 weight percent aluminum chloride hexahydrate at pH values of 3.3±0.5. The components of each of the following emulsions follow.

| | Weight Percent in Emulsion Base | | | | | |
|---|---|---|---|---|---|---|
| | A | B | C | D | E | F |
| Phase I | | | | | | |
| Deionized water to 100 g | q.s. | q.s. | q.s. | q.s. | q.s. | q.s. |
| Phase II | | | | | | |
| Cosmetic emulsion base of Example 2, phase II | 23.58 | 23.58 | 23.58 | 23.58 | 23.58 | 23.58 |
| Phase III | | | | | | |
| Cosmetic emulsion base of Example 2, phase III | 0.45 | 0.45 | 0.45 | 0.45 | 0.45 | 0.45 |
| Phase IV | | | | | | |
| Aluminum chloride hexahydrate | 6.0 | 3.0 | 1.0 | 0.5 | 0.10 | .005 |
| Water | 6.0 | 3.0 | 1.0 | 0.5 | 0.10 | .005 |
| Phase V | | | | | | |
| Sodium hydroxide (50% in water) | q.s. | q.s | q.s. | q.s. | q.s. | q.s. |
| pH | 2.81 | 3.80 | 3.80 | 3.83 | 3.80 | 3.75 |
| Rinse-on Conditioning [a] | | | | | | |
| by Method A | n.d. | d. | d. | d. | d. | n.d. |
| Method B | n.d. | d. | d. | d. | d. | d. |

[a]tested on skin of hands; d. = discernible to touch and n.d. = not discernible.

The data show that the aluminum chloride effectively produces rinse-on conditioning effects at concentrations of from 0.10 to 3.0 weight percent.

When the aluminum salt concentration drops below 0.1 weight percent, rinse-on conditioning is discernible only if tap water and soap is used (Method B).

EXAMPLE 7

The Effect of pH on Rinse-on Conditioning at Various Concentrations of an Aluminum-Zirconium Salt Complex This example shows the conditioning effects produced by varying concentrations of a glycine coordination complex of aluminum zirconium tetrachlorohydrate sold under the trademark, Rezal 36G by Reheis Chemical Company, over a pH range of from about 4 to neutral. The components of each of the following emulsions follow.

| | Weight Percent in Cosmetic Emulsion Base | | | |
|---|---|---|---|---|
| Component | A | B | C | D |
| Phase I | | | | |
| Deionized water to 100 g | q.s. | q.s. | q.s. | q.s |
| Phase II | | | | |
| Cosmetic emulsion base of Example 2, phase II | 23.58 | 23.58 | 23.58 | 23.58 |
| Phase III | | | | |
| Cosmetic emulsion base of Example 2, phase III | 0.45 | 0.45 | 0.45 | 0.45 |
| Phase IV | | | | |
| Rezal 36G (35%) | 1.60 | 1.01 | 0.51 | 0.16 |
| Phase V | | | | |
| Sodium hydroxide (50% in water) | q.s to pH of Formula shown below | | | |

The effect of pH value on discernible conditioning effects produced by the aluminum zirconium complex salt is shown below evaluated by Rinse-on Method A with soft water and Rinse-on Method B with hard water on the skin of the hands.

| Emulsion Formula | pH | Conditioning Produced on Skin of Hands d = discernible to touch n.d. = not discernible | |
|---|---|---|---|
| | | Rinse-on Method A | Rinse-on Method B |
| A-1 | 4.3 | d. | d. |
| A-2 | 5.5 | d. | d. |
| A-3 | 6.7 | d. | d. |
| B-1 | 4.3 | d. | d. |
| B-2 | 5.4 | d. | d. |
| B-3 | 6.5 | d. | d. |
| B-4 | 7.0 | d. | d. |
| C-1 | 4.3 | d. | d. |
| C-2 | 6.0 | n.d. | n.d. |
| C-3 | 7.0 | n.d. | n.d. |
| D-1 | 5.7 | n.d. | d. |
| D-2 | 7.5 | n.d. | n.d. |

The data show that the aluminum zirconium complex produces discernible rinse-on conditioning effects on the skin at concentrations ranging from 0.51 to 1.6 weight percent at a pH value of 4.3. As the pH value increases to 5.5±1, the rinse-on conditioning effects become less discernible and is not discernible when the salt concentration drops below 0.5 weight percent.

EXAMPLE 8

The effect of pH on Rinse-on Conditioning at Various Concentrations of Aluminum Chlorohydrate Emulsions This example shows the rinse-on conditioning effect produced by varying concentrations of aluminum chlorohydrate, at pH values of 4.9±0.7. The components in each of the emulsions follows.

| Component | Weight percent in Cosmetic Emulson Base | | | | |
|---|---|---|---|---|---|
| | A | B | C | D | E |
| Phase I | | | | | |
| Deionized water to 100 g | q.s. | q.s. | q.s. | q.s. | q.s |
| Phase II | | | | | |
| Cosmetic emulsion base of Example 2, Phase II | 23.58 | 23.58 | 23.58 | 23.58 | 23.58 |
| Phase III | | | | | |
| Cosmetic emulsion base of Example 2, Phase III | 0.45 | 0.45 | 0.45 | 0.45 | 0.45 |
| Phase IV | | | | | |
| Aluminum chlorohydrate | 2.44 | 1.22 | 0.61 | 0.185 | 0.12 |
| Deionized water | 2.44 | 1.22 | 0.61 | 0.185 | 0.12 |
| Phase V | | | | | |
| Sodium hydroxide (50% in water) | q.s. to pH shown below | | | | |
| pH | 5.6 | 4.3 | 4.5 | 4.4 | 5.6 |
| Rinse-on Conditioning [a] by | | | | | |
| Method A | d. | d. | d. | d. | n.d |
| Method B | d. | d. | d. | d. | d. |

[a] tested on skin of hands; d = discernible to touch and n.d. = non discernible.

The data show that aluminum chlorohydrate effectively produces rinse-on conditioning effects at concentrations of from 0.12 to 2.44 weight percent, except that, in soft water Method A, conditioning effects drop off at the 0.12 weight percent level.

EXAMPLE 9

The Effect of pH and Concentration on Rinse-on Conditioning of Iron (III)-Containing Emulsions This example shows the rinse-on conditioning effects produced by varying concentrations of iron (III) nitrate, nonahydrate over a pH range of from 1.8 to 8.1. The components of each emulsion follows.

| Component | Weight percent in Cosmetic Emulsion Base | | | |
|---|---|---|---|---|
| | A | B | C | D |
| Phase I | | | | |
| Deionized water to 100 g. | q.s. | q.s. | q.s. | q.s. |
| Phase II | | | | |
| Cosmetic emulsion base of Example 2, Phase II | 23.58 | 23.58 | 23.58 | 23.58 |
| Phase III | | | | |
| Cosmetic emulsion base of Example 2, Phase III | 0.45 | 0.45 | 0.45 | 0.45 |
| Phase IV | | | | |
| Iron (III) Nitrate nonahydrate | 1.70 | 1.00 | 0.50 | 0.17 |
| Water, deionized | 1.70 | 1.00 | 0.50 | 0.17 |
| Phase V | | | | |
| Sodium hydroxide (50% in water) | q.s. to pH shown below | | | |

The effect of pH value on discernible conditioning effects produced by the Iron (III) nitrate salt is shown below as evaluated by Rinse-on Method A and Rinse-on Method B on the skin of the hands.

| Emulsion Formula | pH | Conditioning Produced on Skin of Hands d. = discernible to touch n.d. = not discernible | |
|---|---|---|---|
| | | Rinse-on Method A | Rinse-on Method B |
| A-1 | 1.8 | d. | d. |
| A-2 | 2.5 | d. | d. |
| A-3 | 6.5 | d. | d. |
| A-4 | 8.1 | n.d | d. |
| B-1 | 1.8 | d. | d. |
| B-2 | 2.6 | d. | d. |
| B-3 | 4.6 | d. | d. |
| B-4 | 6.9 | d. (slight) | d. |
| C-1 | 2.2 | d. | d. |
| C-2 | 2.8 | d. | d. |
| D-1 | 2.4 | d. | d. |
| D-2 | 3.0 | d. | d. |

The data show that Iron (III) nitrate produces discernible rinse-on conditioning effects on the skin at concentrations ranging from 0.17 to 1.7 weight percent over a pH range of 1.8 to 6.5. As the pH value increases to 6.9 and above, rinse-on conditioning is less discernible or only discernible when tap water Method B is used.

EXAMPLE 10

The Effect of pH and Concentration on Rinse-on Conditioning of Zirconium (IV)-Containing Emulsions This example shows the rinse-on conditioning effects produced by varying concentrations of zirconium (IV) oxychloride octahydrate over a pH range of from 1.6 to 10.0. The components of each of the emulsions follows.

| Component | Weight percent in Cosmetic Emulsion Base | | | |
|---|---|---|---|---|
| | A | B | C | D |
| Phase I | | | | |
| Deionized water to 100 g. | q.s. | q.s. | q.s. | q.s. |
| Phase II | | | | |
| Cosmetic emulsion base of Example 2, Phase II | 23.58 | 23.58 | 23.58 | 23.58 |
| Phase III | | | | |
| Cosmetic emulsion base of Example 2, Phase III | 0.45 | 0.45 | 0.45 | 0.45 |
| Phase IV | | | | |
| Zirconium (IV) oxychloride octahydrate | 1.33 | 0.80 | 0.40 | 0.133 |
| Water deionized | 1.33 | 0.80 | 0.40 | 0.133 |
| Phase V | | | | |
| Sodium hydroxide (50% in water) | q.s. to pH shown below | | | |

The effect of pH value on discernible conditioning effects produced by the zirconium (IV) salt is shown below as evaluated by Rinse-on Method A with soft water and Rinse-on Method B with hard water on the skin of the hands.

| Emulsion Formula | pH | Conditioning Produced on Skin of Hands d. = discernible to touch n.d. = not discernible | |
|---|---|---|---|
| | | Rinse-on Method A | Rinse-on Method B |
| A-1 | 1.6 | d. | d. |
| A-2 | 3.4 | d. | d. |
| A-3 | 4.4 | d. | d. |
| A-4 | 5.6 | d. | d. |
| B-1 | 1.7 | d. | d. |
| B-2 | 3.0 | d. | d. |
| B-3 | 5.5 | d. | d. |
| B-4 | 10.0 | n.d. | n.d. |
| C-1 | 1.9 | d. | d. |
| C-2 | 4.3 | d. | d. |
| C-3 | 6.7 | n.d. | n.d. |
| D-1 | 2.1 | d. | d. |
| D-2 | 3.5 | n.d. | d. |
| D-3 | 4.0 | n.d. | n.d. |

The data show that the zirconium (IV) oxychloride produces discernible rinse-on conditioning effects on the skin at concentrations ranging from 0.13 to 1.3 weight percent over a pH range 1.6 to 5.6. As the pH value increases above 5.6, rinse-on conditioning is discernible only when tap water Method B is used.

EXAMPLE 11

The Effect of Concentration on Rinse-on Conditioning of Cerium (III)-Containing Emulsions This example shows the rinse-on conditioning effects produced by emulsions containing varying concentrations of cerium (III) nitrate hexahydrate. The components of each of the emulsions follows.

| Component | Weight percent in Cosmetic Emulsion Base | | | |
|---|---|---|---|---|
| | A | B | C[a] | D |
| Phase I | | | | |
| Deionized water to 100 g. | q.s. | q.s. | q.s. | q.s. |
| Phase II | | | | |
| Cosmetic emulsion base of Example 2, Phase II | 23.58 | 23.58 | 23.58 | 23.58 |
| Phase III | | | | |
| Cosmetic emulsion base of Example 2, Phase III | 0.45 | 0.45 | 0.45 | 0.45 |
| Phase IV | | | | |
| Cerium nitrate (III) hexahydrate | 0.50 | 1.0 | 2.0 | 4.0 |
| Deionized water | | | | |
| Phase V | q.s. to pH shown below | | | |
| Sodium hydroxide (50% in water) | | | | |
| pH at 2% Concentration | 6.0 | 6.0 | 6.0 | 6.0 |
| Rinse-on Conditioning[b] by | | | | |
| Method A | d. | d. | d. | d. |
| Method B | d. | d. | d. | d. |

[a]Additional emulsions were prepared similar to Emulsion C, but adjusted to different pH levels. Emulsions $C_1$, $C_2$, $C_3$, and $C_4$ were at pH levels of 2.3, 3.2, 7.0 and 7.5, respectively. These emulsions also produced conditioning discernible to the touch when applied to the hands.
[b]tested on skin of hands; d = discernible to touch.

The data show that cerium (III) nitrate effectively produces rinse-on conditioning effects at concentrations of 0.5 to 4.0 weight percent and at pH level from 2.3 to 7.5.

In a separate experiment, emulsion B is prepared, except that cerium (IV) sulfate salt, is used in place of cerium (III) nitrate at a concentration of 0.65 weight percent. However, no rinse-on conditioning is discerned.

EXAMPLE 12

Effect on Concentration of Water-Soluble Emulsifier on Conditioning With Aluminum-Containing Emulsion This example shows the importance of keeping the concentration of a water-soluble non-ionic emulsifier at a level of 0.5 weight percent or less in an aluminum-containing emulsion for rinse-on conditioning effects.

Emulsion A of Example 1 is prepared, except that a series of emulsions is prepared having a varying concentration of the non-ionic emulsifier, Lipocol C-20, shown below, in Phase II, and the water content in Phase I is reduced accordingly. All compositions have a pH value of 4.0±0.1. Conditioning effects from Rinse-on Method A and Rinse-on Method B are also shown below.

| discernible Emulsion | Weight Percent Non-Ionic Emulsifier | Conditioning Effect on Skin of Hands d. = discernible to touch n.d. = not | |
|---|---|---|---|
| | | Rinse-on Method A | Rinse-on Method B |
| A | 0.18 | d. | d. |
| B | 0.50 | d. | d. |
| C | 1.00 | n.d | d. |
| D | 2.00 | n.d. | n.d. |

The solubility of the non-ionic emulsifier as determined by the well known Hydropbile-Lipophile Balance system, commonly called HLB, has an HLB value of about 15 to 17. It is, therefore, very water soluble. As shown above, the rinse-on conditioning effect produced by the aluminum-containing emulsion drops off as the concentration of the water-soluble emulsifier increases above 0.5 weight percent.

EXAMPLE 13

Skin Protective Barrier Lotion

This example demonstrates the rinse-on conditioning protective barrier effect from an aluminum-containing emulsion.

Emulsion composition A of Example 7 is rubbed onto the wet skin of one hand of a male volunteer using rinse-on Method A. After 5 minutes, the barrier film deposited on the skin is evaluated by placing two drops of an aqueous solution of blue dye (1 weight percent of FD&C Blue #1) on the coated skin area. After 2 minutes, the dye is rinsed from the skin with water. The treated skin area is minimally stained at most, showing that a barrier film is present. In a separate test, a counterpart of emulsion A is prepared without aluminum salt and the volunteer's other hand is treated with this emulsion as above. A pronounced blue stain remains on the skin showing that no barrier film is present.

Similar results were obtained when Emulsion composition A of Example 7 was applied by rinse-on Method B and by rub-on Method C.

EXAMPLE 14

Rinse-on Body Conditioner

This example illustrates a rinse-on body lotion that is used by Rinse-on Method A during a shower bath. The following emulsion is prepared.

| Component | Weight Percent |
| --- | --- |
| Phase I | |
| Deionized water | 75.92 |
| Phase II | |
| Petrolatum | 9.85 |
| Mineral oil 65/75 visc. | 7.45 |
| Lanolin AAA | 0.65 |
| Lipocol C20 | 1.42 |
| Span 60 | 3.31 |
| Methylparaben | 0.15 |
| Propylparaben | 0.10 |
| Phase III | |
| Fragrance | 0.20 |
| 1,3 Dimethyl-5,5-dimethyl-hydantoin | 0.25 |
| Phase IV | |
| Aluminum chloride hexahydrate | 0.30 |
| Deionized water | 0.30 |
| Phase V | |
| Sodium hydroxide (50% in water) to pH 4.0 | 0.10 |
| | 100.00 |

The emulsion provides a non-greasy, moisturizing conditioning effect on the skin.

EXAMPLE 15

Rinse-on After-Shave Conditioner Fragrance

This example illustrates a rinse-on after-shave conditioner fragrance for use after wet or dry shaving. The following emulsion is prepared.

| Component | Weight Percent |
| --- | --- |
| Phase I | |
| Deionized water | 76.30 |
| Phase II | |
| Petrolatum | 9.85 |
| Mineral oil 65/75 visc. | 7.45 |
| Lanolin AAA | 0.65 |
| Span 60 | 4.31 |
| Igepal CO-730 | 0.42 |
| Methylparaben | 0.15 |
| Propylparaben | 0.10 |
| Phase III | |
| Fragrance | 0.50 |
| 1,3 Dimethyl-5,5-dimethyl-hydantoin | 0.25 |
| Phase IV | |
| Sodium hydroxide (50% in water) to pH 4.0 | 0.02 |
| | 100.00 |

The facial beard of a male volunteer is wet-shaved in the usual manner with a commercial shave cream and safety razor. All remaining shave cream is rinsed off with water and the skin is lightly blotted. The after-shave conditioner fragrance is rubbed onto the wet shaved skin area. The skin is rinsed with water and blotted. The shaved skin area is smooth, conditioned and fragranced and the fragrance lasts several hours.

EXAMPLE 16

Rub-on Shave Lotion

The conditioner composition (D) of Example 9 is rubbed onto a hairy portion of the lower leg area of a female volunteer. The treated leg area is then shaved with a safety razor. The shaved area is water rinsed and blotted dry. The skin is smooth, conditioned and moisturized.

In a second test, the conditioner composition is rubbed onto the hairy armpit area of a female volunteer. The armpit is shaved in the usual manner with a safety razor and the shaved area is rinsed with water. The shaved skin is smooth and conditioned.

EXAMPLE 17

Rub-on Hot Oil Conditioner

Conditioner (A) of Example 5 is rubbed onto the freshly washed hair of a female volunteer whose hair history includes frequent chemical dyeing and waving treatments. The conditioner is thoroughly rubbed into the hair and scalp, the hair is covered with a plastic cap and the covered hair is heated under a salon-style hair dryer at a hot setting for 15 minutes. The hair is rinsed with water, blotted and dried in the usual manner. The hair is smooth and conditioned.

The present invention has been described with respect to preferred embodiments. It will be clear to those skilled in the art that modifications and/or variations of the disclosed compositions and methods can be made without departing from the scope of the invention set forth herein. The invention is defined by the claims that follow:

What is claimed is:

1. A hair and skin conditioning composition comprising an oil-in-water emulsion including:
   (a) about 70 to about 90 weight percent water;
   (b) about 5 to about 25 weight percent water-insoluble, unctuous oleaginous material;
   (c) as the sole emulsifying agent in the composition, about 0.1 to about 7 weight percent of a water-dispersible emulsifying agent selected from the group consisting of non-ionic and cationic emulsifiers, and mixtures thereof; wherein the water-dispersible emulsifying agent does not form a true solution in water;

(d) about 0.05 to about 3.0 weight percent water-dispersible, non-toxic hydrated polyvalent metal salt having a cation selected from the group consisting of aluminum (III), cerium (III), iron (III), zirconium (IV), aluminum zirconium coordination complexes and mixtures thereof; and (e) sufficient acid or alkali to provide a pH value of about 1.5 to about 7.5;

said emulsion being adapted to invert to a water-in-oil emulsion when rubbed onto skin and hair to provide a moisturizing, conditioning, protective barrier on said skin and hair.

2. The composition of claim 1, wherein the oleaginous material is selected from the group consisting of mineral hydrocarbon waxes, greases and oils; animal fats and greases; plant waxes; saturated and unsaturated vegetable and animal oils; hydrogenated unsaturated oils, waxes and fats; non-volatile linear polysiloxane polymer and an olefinic ester of saturated fatty acid; and mixtures thereof.

3. The composition of claim 1, wherein the emulsifying agent is a cationic material selected from the group consisting of quaternized ammonium bromide and chloride salts and mixtures thereof.

4. The composition of claim 1, wherein the emulsifying agent includes a water-soluble non-ionic material.

5. The composition of claim 1 wherein the metal salt is aluminum chloride hexahydrate present in amounts of from 0.05 to about 3 weight percent in a composition having a pH value in a range of from about 1.5 to about 5.

6. The composition of claim 1 wherein the metal salt is aluminum chlorohydrate present in amounts of from 0.12 to about 2.5 weight percent in a composition having a pH value in a range of from 4.2 to about 5.6.

7. The composition of claim 1 wherein the metal salt is zirconium (IV) oxychloride octahydrate present in amounts of from 0.13 to about 1.3 weight percent in a composition having a pH value in a range of from 1.6 to about 5.6.

8. The composition of claim 1 wherein the polyvalent metal salt is a loosely hydrated coordination complex of aluminum zirconium chlorohydrate, including the tri-, tetra-, and pentachlorohydrates and glycine complexes thereof, present in amounts of from 0.51 to about 1.6 weight percent in a composition having a pH value in a range of from 4.3 to about 7.0.

9. The composition of claim 1 wherein the polyvalent metal salt is the nonahydrate salt of iron (III) nitrate present in amounts of from 0.17 to about 1.7 weight percent in a composition having a pH value in a range of from 1.8 to about 6.5.

10. The composition of claim 1 wherein the polyvalent metal salt is the hexahydrate salt of cerium (III) nitrate present in amounts of from 0.5 to about 4.0 weight percent in a composition having a pH value in a range of from 2.3 to about 7.5.

11. A hair and skin conditioning composition comprising an oil-in-water emulsion including;

(a) about 70 to about 90 weight percent of water;

(b) about 5 to about 25 weight percent of unctuous oleaginous material selected from the group consisting of petrolatum, mineral oil, hydrogenated triglyceride, vegetable oil, animal grease, aliphatic fatty alcohol, olefinic esters of saturated fatty acid, and non-volatile linear polysiloxane polymer;

(c) about 0.1 to about 7 weight percent of a non-ionic emulsifying agent as the sole emulsifying agent in the composition;

(d) about 0.05 to about 3 weight percent water-dispersible, non-toxic, hydrated polyvalent metal salt having a cation selected from the group consisting of aluminum (III), zirconium (IV), cerium (III), iron (III), aluminum zirconium coordination complexes and mixtures thereof;

(e) sufficient acid or alkali to provide a pH value of about 1.5 to about 7.5.

12. The composition of claim 11 wherein the emulsifying agent further includes at least one cationic emulsifying agent selected from the group consisting of quaternized ammonium bromide and chloride salts and mixtures thereof.

13. The composition of claim 3 wherein the cationic emulsifying agent is cetyltrimethylammonium chloride.

14. The composition of claim 11 wherein the polyvalent metal salt is the hexahydrate of aluminum chloride, said composition having a pH value of from about 2.0 to about 5.0.

15. A method of providing a moisturizing, conditioning and protective barrier on the skin comprising the steps of rubbing the composition of claim 1 onto wet skin; and rinsing the skin with water; and drying the rinsed skin.

16. A method of providing a moisturizing, conditioning and protective barrier on the skin comprising the steps of rubbing the composition of claim 1 onto dry skin; and rubbing the composition into the skin.

17. A method of providing a moisturizing, conditioning and protective barrier on the hair comprising the steps of rubbing the composition of claim 1 onto wet hair; rinsing the hair with water; and drying the rinsed hair.

18. The composition of claim 1 wherein the composition further includes an ultraviolet absorbing sunscreen agent.

19. In a method for conditioning the hair by contacting the hair with an oily conditioner composition and heating the hair for providing a hot oil treatment and thereafter rinsing the hair with water, the improvement comprising contacting the hair with the composition of claim 1 as said oily conditioner.

20. In a method for conditioning the hair by contacting the hair with an oily conditioner composition and heating the air for providing a hot oil treatment and thereafter rinsing the hair with water, the improvement comprising contacting the hair with the composition of claim 11 as said oily conditioner.

* * * * *